United States Patent [19]

Argese et al.

[11] Patent Number: 6,013,793
[45] Date of Patent: Jan. 11, 2000

[54] PROCESS FOR THE PREPARATION OF TETRAAZAMACROCYCLES

[75] Inventors: Maria Argese; Giorgio Ripa; Alessandro Scala; Vittorio Valle, all of Milan, Italy

[73] Assignee: Dibra S.p.A., Italy

[21] Appl. No.: 09/203,604

[22] Filed: Dec. 2, 1998

Related U.S. Application Data

[62] Division of application No. 08/878,508, Jun. 19, 1997.

[30] Foreign Application Priority Data

Jun. 21, 1996 [IT] Italy .................................. MI96A1257

[51] Int. Cl.[7] ................................................. C07D 255/02
[52] U.S. Cl. ......................... 540/474; 540/472; 528/342; 528/343
[58] Field of Search ................................. 540/472, 474; 528/342, 343

[56] References Cited

U.S. PATENT DOCUMENTS 5,587,451  12/1996  Athey et al. ............................ 528/345

FOREIGN PATENT DOCUMENTS

96/28432  9/1996  United Kingdom .
Wo 96/28432  9/1996  WIPO .

OTHER PUBLICATIONS

Weisman et al., Tetrahedron letters, vol. 21, pp. 335–338, 1980.

*Primary Examiner*—Mukund J. Shah
*Assistant Examiner*—Pavanaram K Sripada
*Attorney, Agent, or Firm*—Nixon & Vanderhye

[57] ABSTRACT

A process for the preparation of tetraazamacro-cycles of general formula (I)

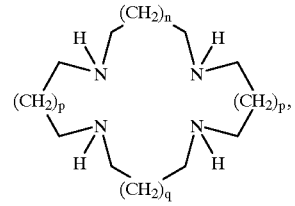

wherein n, p and q can independently be 0 or 1, comprising the following steps:

a): condensation of polyamines with a glyoxal derivative;

b): condensation of the resulting compound with an alkylating agent;

c): oxidation of the resulting compound with an oxidizing agent, to give a mixture of oxidated products which is submitted to d): hydrolysis in acid aqueous solution, to give the compound of formula (I).

7 Claims, No Drawings

PROCESS FOR THE PREPARATION OF TETRAAZAMACROCYCLES

This application is a division of Ser. No. 08/878,508 filed on Jun. 19, 1997.

This invention refers to a process for the preparation of tetraazamacrocycles of general formula (I)

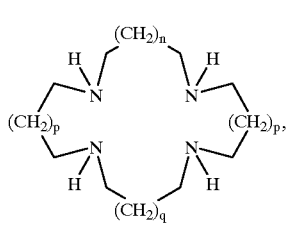

wherein n, p and q can independently be 0 or 1, comprising the following steps of Scheme 1:

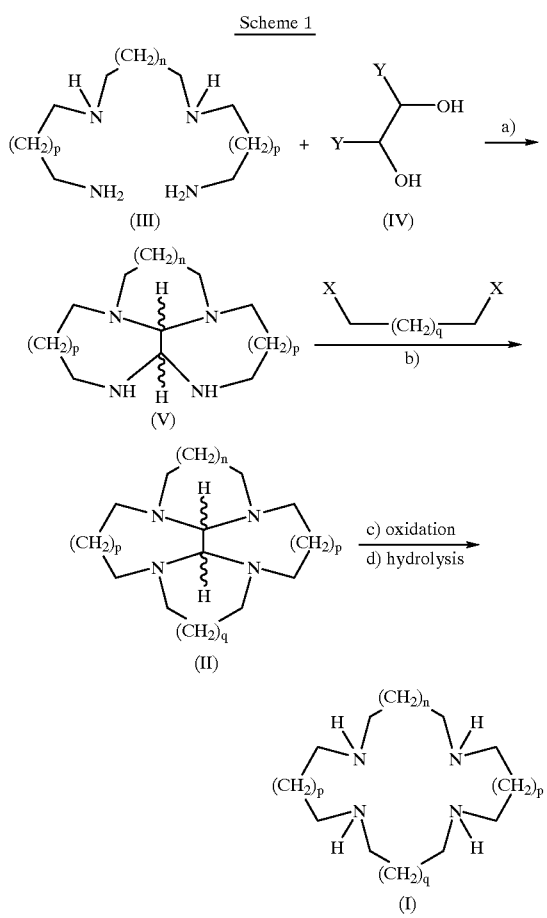

wherein
- step a): condensation of polyamines of formula (III) with the glyoxal derivative of formula (IV), wherein Y is —OH (glyoxal hydrate) or [—S$_3$Na$^+$] (Bertagnini's salt), in water or in water-soluble solvents or mixture thereof, at 0–50° C., in the presence of stoichiometric amounts or of a slight excess of calcium hydroxide, to give the compound of formula (V);
- step b): condensation of the compound of formula (V) with an alkylating agent X—CH$_2$—(CH$_2$)$_q$—CH$_2$—X, wherein q is as previously defined and X is a halogen or a sulfonic acid reactive derivative, in at least stoichiometric amounts, in the presence of at least 2 moles of a base selected from alkali or alkaline-earth metal carbonates per mol of compound (V), at 25–150° C., to give the compound of formula (II);
- step c): oxidation of the compound of formula (II) with an oxidizing agent, in water or in a diphasic system constituted by water and an organic solvent, resistant to oxidation, at 0–100° C., to give a mixture of oxidized products which is submitted to
- step d): hydrolysis in acid aqueous solution at a pH lower than 2 or in a basic aqueous solution at a pH higher than 12, at 110–200° C., to give the compound of formula (I).

and, in particular, the process for the preparation of 1,4,7,10-tetraazacyclododecane (known as Cyclen) of formula (VIII), where in the compound of formula (I) n, p and q are 0, according to the steps of Scheme 2.

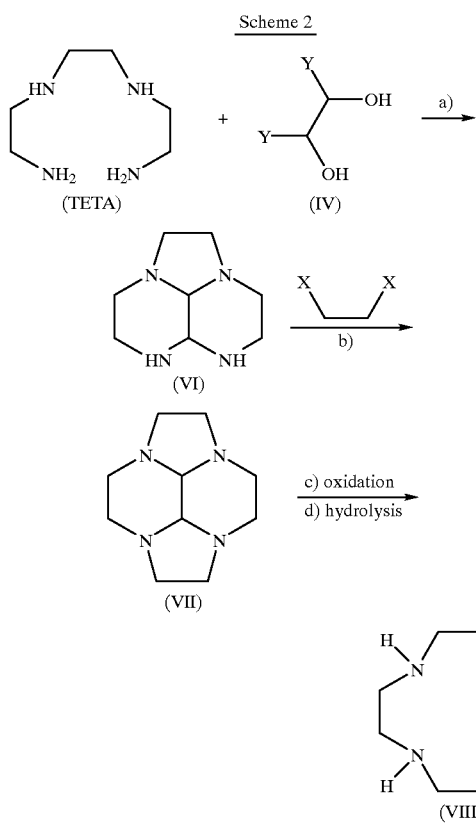

1,4,7,10-tetraazacyclododecane is the precursor for the synthesis of macrocyclic chelating agents for metal ions, since these chelating agents form stable complexes with such ions.

In particular the complexes with paramagnetic metal ions, especially gadolinium ion, of such chelates are useful in the medical diagnostic field through Magnetic Resonance Imaging (MRI), otherwise troublesome due to the high toxicity of the free ion. Presently two contrast media are available on the market, Dotarem($^R$) and Prohance($^R$), two gadolinium complexes whose chemical structure is based on Cyclen, while others are still under investigation.

Therefore it is important to work out a synthetic method relying on this "building block", which is cost-effective even from an industrial point of view.

The process of this invention uses as raw materials linear polyamines, glyoxal, alkyl dihalides, which are generally economical, and a suitable oxidizing agent.

Therefore, the synthetic process is at the same time advantageous from an economic and environmental point of view, since it does not require the preparation of amines tosylderivatives, commonly used in the traditional synthesis of Richman-Atkins (see J. Am. Chem, Soc., 96, 2268, 1974).

The key intermediate of the new process is the tetracyclic derivative of general formula (II):

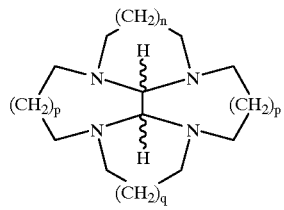
(II)

where n, p and q are as previously defined, and the two hydrogen atoms bound to the carbon atoms of the bridge can generate cis or trans configurations, according to the size of the tetracyclic derivative.

Particularly useful is the intermediate of formula (VII) for the preparation of 1,4,7,10-tetraazacyclododecane.

Such products have been already described in literature. For instance in G. R. Weisman, S. C. H. Ho, V. Johnson, Tetrahedron Lett., 1980, 21, 335, the synthesis of the following tetracycles (see Table 1), has been described without mentioning their use, but with the aim of studying the stereochemistry of the central bond.

TABLE 1

| n | p | q | |
|---|---|---|---|
| | | | 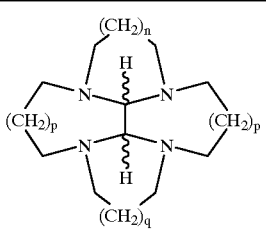 |
| 0 | 0 | 0 | 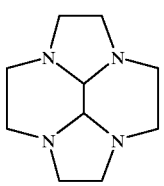 |
| 1 | 0 | 0 | 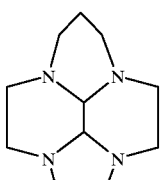 |

TABLE 1-continued

| n | p | q | |
|---|---|---|---|
| | | | 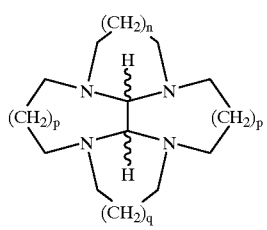 |
| 1 | 0 | 1 | 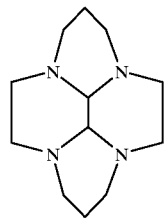 |
| 1 | 1 | 1 | 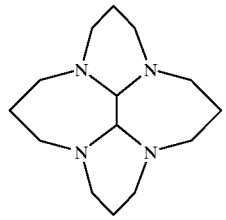 |

In addition the bibliographic references cite other syntheses starting from polyazamacrocycles and glyoxal, in aqueous solution or in dipolar aprotic solvents, such as acetonitrile, see for instance the following publications:

W. Choinski, R. A. Kolinski, Polysh. Pat. 101075, Chemical Abstracts. 1980, 92, 94444x; p1 R. A. Kolinski, F. G. Riddel, Tetrahedron Lett. 1981, 22, 2217.

A principal characteristic of the compounds of formula (II), also cited in the above works, is the extraordinary stability under basic or acid hydrolytic conditions and with respect to reducing agents, differing from non-cyclic aminals. This stability excluded, up to now, the possibility of using the above tetracycles as direct precursors of polyazamacrocycles, and in some references the use of the same tetraazamacrocycle of formula (I) is required as raw material (G. R. Weisman, S. C. H. Ho, V. Johnson, Tetrahedron Lett., 1980, 21, 335).

More recently, WO96/28432 describes a synthetic process for compound (VII), according to the following reaction scheme:

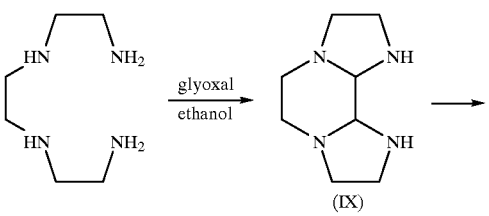
(IX)

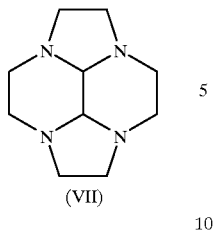

(VII)

The structure of the intermediate of formula (IX) is different from the intermediate of formula (VI), whose synthesis has been previously illustrated and is part of this invention (cfr. Example 1B experimental section). In fact it has a structure constituted by three cycles 5,6,5 (the numbers stand for the number of atoms constituting the ring of the tricyclic system).

As a matter of fact, the synthetic conditions of the compound of formula (IX) described in WO96/28432 do not correspond to those of the intermediate (VI) of this invention, which require the use of calcium hydroxide.

WO 96/28432 also states that the intermediate (VII) can be converted into 1,4,7,10-tetraazacyclododecane (VIII) through acid hydrolysis, for instance with hydrobromic acid, or through heating with hydroxylamine in ethanol.

The hydrolytic treatment with hydrobromic acid, disclosed in the experimental section of WO 96/28432, appears in conflict with the teaching of literature, which indicate the unexpected stability of (II) in acid aqueous solutions (cfr. Weisman, Tetr. Lett., 1980, 21, 335).

The reaction with hydroxylamine in ethanol, according to WO 96/28432, requires the use of strong excesses of hydroxylamine as free base. These conditions, implementable on a laboratory scale, are not suitable for an industrial process, due to hydroxylamine dangerousness, which requires extremely careful handling, use and discharge.

Now, it has been surprisingly found that the compounds of formula (II), which underwent oxidation with a suitable oxidizing agent, give a mixture of products which, despite of the starting compound, are convertible into tetraazamacrocycle of formula (I) through a simple hydrolysis.

These conditions are extremely advantageous even on an industrial scale, since they can exploit ecological, economical and low-risk processes.

Therefore this invention refers to a new process for the preparation of tetraazamacrocycles of general formula (I)

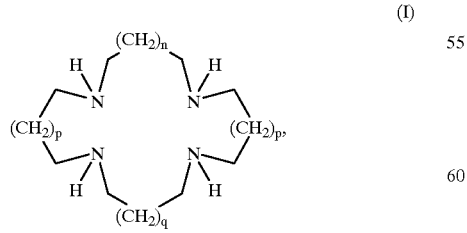

(I)

wherein n, p and q can independently be 0 or 1, comprising the following steps of Scheme 1:

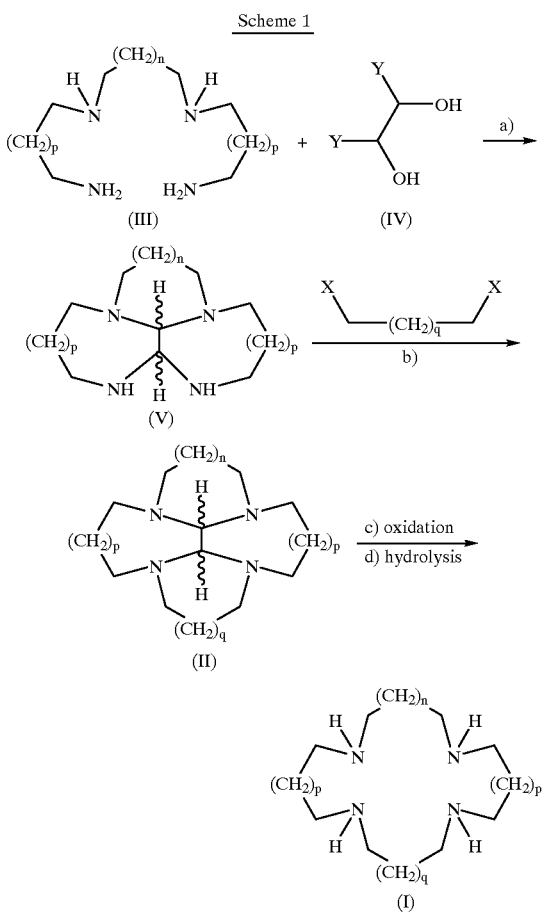

wherein
step a): condensation of polyamines of formula (III) with the glyoxal derivative of formula (IV), wherein Y is —OH (glyoxal hydrate) or [—SO$_3$—Na$^+$] (Bertagnini's salt), in water or in water-soluble solvents or mixture thereof, at 0–50° C., in the presence of stoichiometric amounts or of a slight excess of calcium hydroxide, to give the compound of formula (V);

step b): condensation of the compound of formula (V) with an alkylating agent X—CH$_2$—(CH$_2$)$_q$—CH$_2$—X, wherein q is as previously defined and X is a halogen or a sulfonic acid reactive derivative, in at least stoichiometric amounts, in the presence of at least 2 moles of a base selected from alkali or alkaline-earth metal carbonates per mol of compound (V), at 25–150° C., to give the compound of formula (II);

step c): oxidation of the compound of formula (II) with an oxidizing agent, in water or in a diphasic system constituted by water and an organic solvent, resistant to oxidation, at 0–100° C., to give a mixture of oxidized products which is submitted to step d): hydrolysis in acid aqueous solution at a pH lower than 2 or in a basic aqueous solution at a pH higher than 12, at 110–200° C., to give the compound of formula (I).

Preferred is the process of this invention for the preparation of: 1,4,7,10-tetraazacyclotridecane, where in the compound of formula (I) n is 1 p and q are both 0; 1,4,8,11-tetraazacyclotetradecane, where in the compound of formula (I) n is 0, p is 1 and q is 0; 1,4,8,12- tetraazacyclopentadecane, where in the compound of formula (I) n is 1 p is 1 and q is 0. Particularly preferred is the process of this invention for the preparation of 1,4,7,10-tetraazacyclododecane (known as Cyclen) of formula (VIII), where in the compound of formula (I) n, p and q are equal to 0, according to the following scheme through the preparation of intermediate 3H,6H—2a,5,6,8a-octahydro-tetraazacenaphthylene of formula (VI) starting from triethylentetraamine (TETA; corresponding to the compound of formula (III) when n=p=0) and the following preparation of intermediate 2a,4a,6a,8a-decahydro-tetraazacyclopent[fg]acenaphthylene of formula (VII).

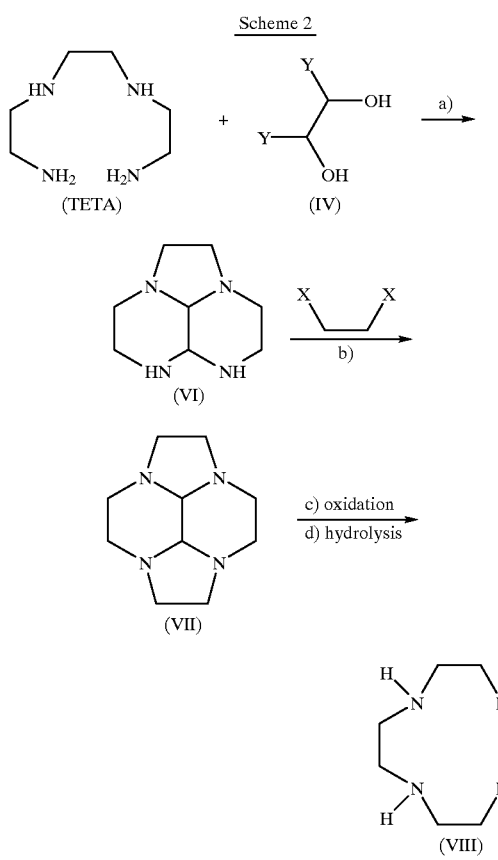

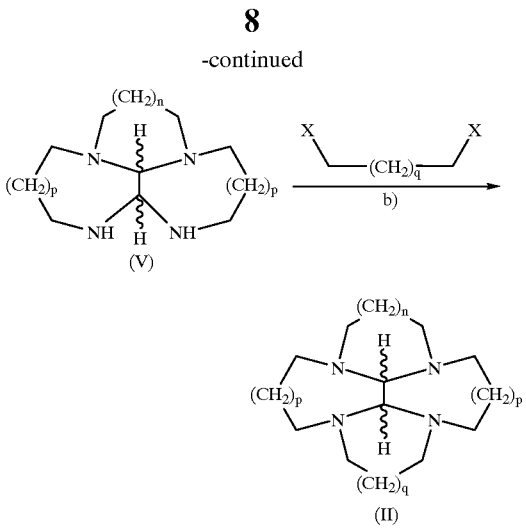

Preferred is the process for the preparation of compounds selected from the group constituted by: 2a,4a,6a,8a-decahydro-tetraazacyclopent[fg]acenaphthylene, where n, p and q are 0 in the compound of formula (II); 7H—2a,4a,6a,9a-decahydro-tetraazacyclohept[jkl]-as-indacene, where n is 1, p and q are both 0 in the compound of formula (II); 1H,6H9H—3a,5a,8a,10a-decahydro-tetraazapyrene, wherein is 0, p is 1 and q is 0 in the compound of formula (II); 1H,6H,9H—3a,5a,8a,11a-decahydro-tetraazacyclohepta[def]phenantrene, where n is 1, p is 1 and q is 0 in the compound of formula (II).

Particularly preferred is the synthesis of 2a,4a,6a,8a-decahydro-tetraazacyclopent[fg] acenaphthylene useful for the synthesis of 1,4,7,10-tetraazacyclododecane.

Another aspect of this invention is an alternative synthesis of the compounds of formula (II), when n is equal to q, to give the compounds of formula (X), starting from linear diamines of formula (XI) where n is not present, as in Scheme 4:

This invention also refers to a synthetic process useful for the preparation of tetracyclic compounds of formula (II), comprising only steps a) and b) of Scheme 1, according to the following Scheme 3:

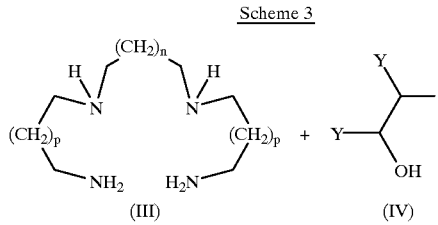

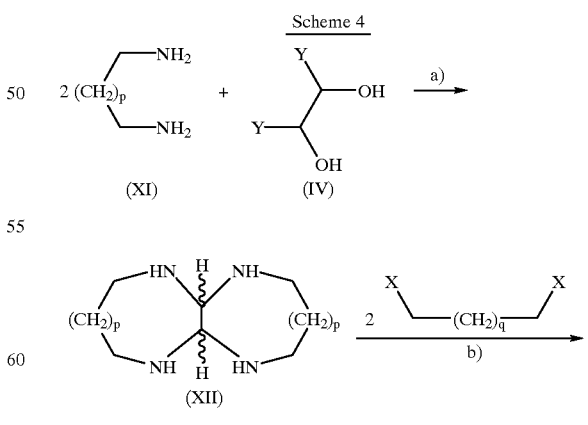

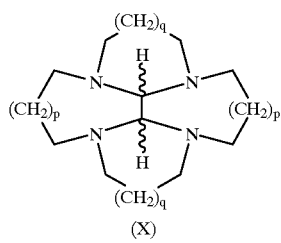

(X)

comprising steps a) and b), as from Scheme 1, with a difference in the amounts of reactives which are added as indicated in Scheme 4 or in slight excess.

As far as step b) is concerned, according to the process of Scheme 1 and 4, and in the case q is 0, the solvent can be even 1,2-dichloroethane (also acting as reactive).

The alkylating agent in step b), as previously said, is a dihalide or a diol, in which the hydroxy groups have been derivatized as reactive esters of sulfonic acid (for instance tosylates, mesylates, nosylates).

The alkylating agent is dosed in amounts of at least 1 mol per mol of intermediate of formula (V), or at least 2 moles per mol of intermediate of formula (XII).

The reaction is carried out in the presence of an inorganic base, preferably an alkali metal carbonate, dosed in amounts of at least 2 moles per mol of alkylating agent.

The temperature, according to the solvent and the alkylating agent, can range between 25 and 150° C., preferably 50–80° C. Reaction time is 1–48 h.

When the cyclization ends, the suspension is cooled and the insoluble salts are filtered.

The filtrate is concentrated to a residue and the compound of formula (II) or the analogous compound of formula (X) is extracted by using an apolar solvent (as hexane or toluene). The product is concentrated to a solid residue to give the compounds of formula (II) for Scheme 1 or formula (X) for Scheme 4.

For the oxidation of compounds of formula (II) and (X), according to step c) of Scheme 1, the usual oxidizing agent cited in literature can be used for the oxidation of aliphatic amines (J. March, Advanced Organic Chemistry, Wiley-Interscience), such as:

derivatives of transition metals with a high level of oxidation, such as potassium permanganate;
  derivatives of halogens with positive oxidation state, such as sodium hypochlorite;
  halogens, such as bromine and chlorine;
  peroxides, such as hydrogen peroxide;
  peracid salts, such as sodium persulfate;
  oxygen: in acid solution and in particular in concentrated sulfuric acid solution.

Other possibilities are the use of metal salts, such as iron trichloride, combined with oxygen.

In addition to the usual oxidizing agents, substances which are known as reducing agents can be used. These substances with respect to compounds (II) and (X) surprisingly act as oxidizing agents. A typical example is the use of sodium bisulfite in slightly acidic or neutral solution.

Usually the oxidation is performed in water, but with certain oxidizing agents, an organic solvent can be added (for instance acetic acid with bromine), under the conditions described in literature (for instance Deno et al., J. Am. Chem. Soc., 1968, 3502). The pH depends on the oxidizing agent: for instance, permanganate generally reacts in neutral or slightly basic solutions, while iron trichloride and oxygen react in acid or highly acid solutions.

Even temperatures and reaction times depend on the oxidizing agent. The mildest conditions involve the use of permanganate in water (1–2 h at 0–10° C.), while the use of hydrogen peroxide or hypochlorite (approx. 48 h, 100° C.) requires drastic conditions.

The oxidation of compounds (II) and (X) usually generates an extremely unstable dihydroxyl derivative, bringing about a conversion into other products through rearrangement reactions and other possible oxidations, as illustrated in the following Scheme 5 in the case of 2a,4a,6a,8a-decahydrotetraazacyclopent[fg]acenaphthylene (VII):

Scheme 5

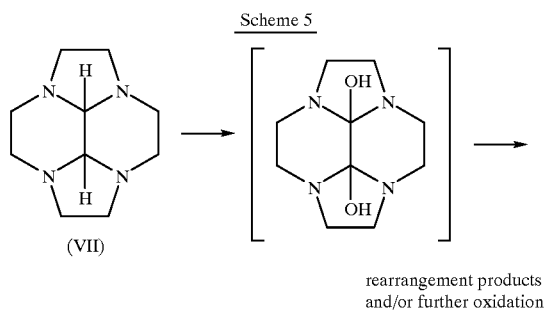

rearrangement products and/or further oxidation

In particular, during the oxidations of compound (VII) with bromine in slightly acidic solution, the dihydroxylate derivative is converted into a product with a dicationic structure of formula (XIII), which is isolated as perchlorate salt of formula (XIV), nearly water-insoluble, through addition of perchlorate ions to the solution of oxidation (see Experimental Section):

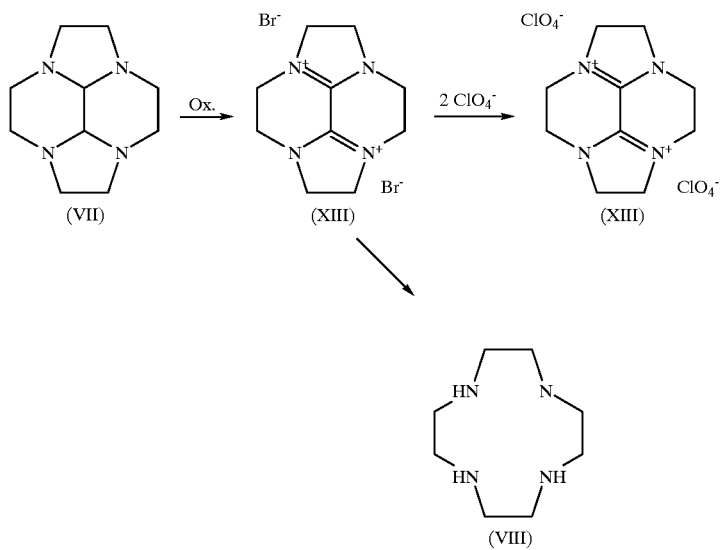

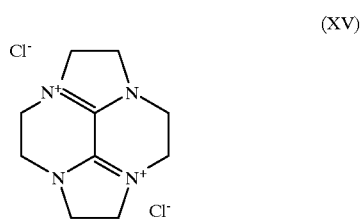

Other salts can be prepared from compound of formula (XIV) through ion exchange processes: for instance, through elution of an aqueous solution of compound (XIV) on a column of an anion-exchange resin (Cl⁻ form), for example Amberlite 4200, a solution is obtained containing compound (XV) which can be isolated from isopropanol.

(XV)

In the first oxidative step, 4 electrons play a definitive role, while the number of electrons which takes part into other oxidation process is unknown.

For a complete oxidation of the tetracycle intermediate, the amount of oxidizing agent should grant the extraction of at least 4 electrons, plus a possible excess, which can be determined experimentally. Since the aim of the reaction is not the completion of tetracycle oxidation, but the highest production of the effective tetraazamacrocyle precursors, it is necessary, in some case, to stop the oxidation before the total tetracycle disappearance.

Table 2 illustrates some examples of oxidation of 2a,4a, 6a,8a-decahydro-tetraazacyclopent[fg]acenaphthylene to give 1,4,7,10-tetraazacyclododecane.

TABLE 2

Preparation of 1,4,7,10-tetraazacyclododecane through oxidation of 2a,4a,6a,8a-decahydro-tetraazacyclopent[fg]acenaphthylene in aqueous solution

| Oxidizing agent | moles | t (h) | T (° C.) | Oxidation (%) | Yield (%) |
|---|---|---|---|---|---|
| Permanganate | 1,33 | 2 | 0 | 70 | 43 |
| Permanganate | 2 | 1 | 10 | 100 | 52 |
| Hypochlorite | 6 | 24 | 80 | 63 | 38 |
| Hypochlorite | 12 | 48 | 80 | 100 | 27 |
| Persulfate | 2 | 1 | 0 | 58 | 33 |
| Persulfate | 2.5 | 2 | 0 | 85 | 38 |
| Bromine | 2.5 | 18 | 20 | 99 | 62* |

*after recrystallization from toluene (1st crop)

The last two columns from right show the tetracycle oxidation percentage and the final yield in 1,4,7,10-tetraazacyclododecane, isolated after hydrolysis of the mixture resulting from the final oxidation (insoluble inorganic compounds, such as manganese dioxide, are removed by filtration).

In case of oxidation carried out under neutral or slightly basic conditions, the hydrolysis is carried out in a highly basic aqueous solution (pH >12), at a temperature ranging from 110 to 200° C., and during 3 and 24 h.

The isolation of 1,4,7,10-tetraazacyclododecane is carried out through crystallization of the same from the suitably concentrated hydrolyzed solution.

In case of oxidation carried out in acid solution, in alternative to the conditions of basic hydrolysis, acid hydrolysis can be performed, operating for instance for 5–48 h in sulfuric acid-water, at 100–150° C.

When the acid hydrolysis is complete, the solution is alkalinized, and after concentration, 1,4,7,10-tetraazacyclododecane is isolated through crystallization. The product can be recrystallized from water, toluene or ethyl acetate.

Particularly preferred is the preparation of 1,4,7,10-tetraazacyclododecane, according to the previously cited Scheme 2, using bromine, as oxidizing agent in step c), in aqueous solution at a pH of 4–6, preferably 4.5, in a ratio of 2.0–3.0 moles per mol of compound (VII), preferably 2.5 and at a temperature of 17–30° C.

As various changes could be made in the above compositions and methods without departing from the scope of the invention, it is intended that all matter contained in the above examples shall be interpreted as illustrative and not in a limiting sense.

The following gas-chromatographic method has been used to monitor the reactions (except for the compound of formula (XIII))

Equipment: gas-chromatographic unit Hewlett-Packard series 5890 II Plus equipped with self-sampling unit series 7673 and unit HP-3365

Column: silica capillary 25 m, int. diam. 0.32 mm, stationary phase CP Sil 19CB, film thickness 0.2 mm (Chrompack art.7742)

Oven temperature: first isotherm at 120° C. for 5 min; ramp 15° C./min; final isotherm at 260° C. for 2 min Injected volume: 1 mL Detector: FID; temperature 275° C.

EXAMPLE 1

Preparation of 2a,4a,6a, 8a-decahydro-tetraazacyclopent[fg]acenaphthylene (CAS RN 74199-09-0) according to Scheme 1.

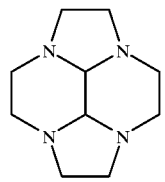

A) Triethylenetetraamine hydrate 520g of triethylenetetraamine (GC 62% % in area) are dissolved in 800 mL of toluene. 80 mL of water are added under stirring, then the solution is cooled to 25° C. and germinated with purified triethylenetetraamine. The suspension is kept under stirring for 45 min. at 20° C., then cooled to 5–10° C. for 1 h. The crystallized solid is filtered, washed with few toluene and dried at 30° C. under vacuum for 8 h to give 365 g of the desired product. Yield: 91% Water content: 17% GC: 97% (%in area)

B) 3H,6H—2a,5,6,8a-Octahydro-tetraazacenaphthylene (CAS RN 78695-52-0)

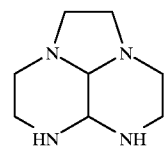

To a solution of triethylenetetraamine hydrate (100 g, 0.54 mol) in water (1 L) 80 g (1.08 mol) of calcium hydroxide are added. The suspension is cooled to 5° C., then a 5%-glyoxal aqueous solution (626 g, 0.54 mol) is added under stirring. After 2 h the reaction is complete (no triethylenetetraamine, GC analysis). The solution is taken to 20° C., the insoluble inorganic solid is filtered and washed with water. The filtrate is concentrated in a rotating evaporator under vacuum to give 100 g of the desired intermediate as colorless oily liquid. (GC purity: >75%)

Note: the intermediate of formula (VI) can be purified through the preparation of salts. For instance, 15 g (0.09 mol) of the compound (VI) are dissolved in 100 g of toluene. 5.5 g of 96% acetic acid are added. After 10 min under stirring the precipitate is filtered and washed with few toluene and dried to 30° C. under vacuum to give 14.1 g of (V) monoacetate. Yield: 70%. GC: >98% $^1$H—NMR, $^{13}$C—NMR, IR and MS spectra are consistent with the structure.

C) 2a,4a,6a,8a-Decahydro-tetraazacyclopent[fg]acenaphthylene (CAS RN 79236-92-3)

The crude intermediate (VI) is redissolved in 1 L of DMAC. 101.4 g (0.54 mol) of 1,2-dibromoethane are added. The resulting solution is dropwise added to a suspension constituted by anhydrous sodium carbonate (600 g) and DMAC (1 L), then heated to 100° C. When the 20-min addition ends, the suspension reacts for additional 30 min. The inorganic salts can filtered and the filtrate is concentrated in a rotating evaporator under vacuum, up to a residue, which is dissolved to 0.5 L of hexane. The insoluble by-products are filtered, and the filtrate is concentrated to dryness to give 48 g (0.24 mol) of the desired product. Yield: 45% GC: 98.5% (% in area) $^1$H—NMR, $^{13}$C—NMR, IR and MS spectra are consistent with the structure.

EXAMPLE 2

Preparation of 2a,4a,6a,8a-decahydro-tetraazacyclopent[fg]acenaphthylene according to Scheme 1, using 1,2-dichloroethane

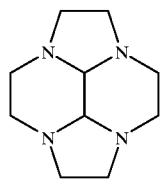

80 g (0.48 mol) of crude 3H,6H-2a,5,6,8a-tetraazanaphthylene octahydrate (prepared according to Example 1) are dissolved in 0.4 L of 1,2-dichloroethane. 100 g of anhydrous sodium carbonate are added and the suspension is heated to 50° C. for 48 h and cooled. The insoluble product is filtered and the filtrate is concentrated to dryness. The compound of formula (VII) is extracted with 0.4 L of hexane. The insoluble product is filtered and the filtrate is concentrated to give 31.2 g (0.16 mol) of the desired product. Yield: 33%. GC: 97.5% (%in area) $^1$H—NMR, $^{13}$C—NMR, IR and MS spectra are consistent with the structure.

Following the procedure of the example the following tetraazacycles are prepared:

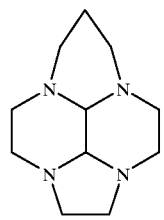

7H—2a,4a,6a,9a-decahydro-tetraazacyclohept[jkl]-as-indacene (CAS RN 74199-11-4) starting from N,N'-bis(2-aminoethyl)-1,3-propanediamine (commercial product, CAS RN 4605-14-5)

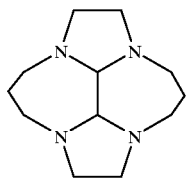

1H,6H-3a,5a,8a,10a-decahydro-tetraazapyrene (CAS RN 72738-47-7) starting from N,N'-bis(3-aminopropyl) ethylenediamine (commercial product, CAS RN 10563-26-5)

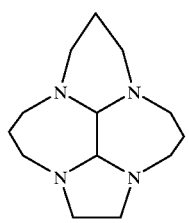

1H,6H,9H-3a,5a,8a,11a-decahydro-tetraazacyclohepta-[def]phenantrene starting from N,N'bis-(3-aminopropyl)-1,3-propanediamine (commercial product, CAS RN 4741-99-5)

EXAMPLE 3

Preparation of 2a,4a,6a,8a-decahydro-tetraazacyclopent[fg]acenaphthylene according to Scheme 4

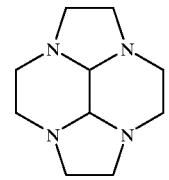

To an aqueous solution of ethylenediamine (60.1 g, corresponding to 1 mol) in water (300 mL) 72.6 g (0.5 mol) of 40%-glyoxal aqueous solution are added and kept at room temperature (25° C.) for an entire night. The solution is concentrated in a rotating evaporator under vacuum, up to a residue. The solid residue is suspended in 900 mL of DMAC, 500 g of anhydrous sodium carbonate are added and a solution of 187.87 g (1 mol) of 1,2-dibromoethane in DMAC (500 mL) is dropwise added. The suspension is heated to 40° C. and kept under reaction for 48 h. The insoluble salts are filtered and the filtrate is concentrated in a rotating evaporator under vacuum, up to a residue, which is added with 0.5 L of hexane. The insoluble product is filtered and concentrated to dryness to give 38 g (0.19 mol) of the desired product. Yield: 38% GC: 98.0% (%in area) $^1$H—NMR, $^{13}$C—NMR, IR and MS spectra are consistent with the structure.

EXAMPLE 4

Preparation of 1,4,7,10-tetraazacyclododecane through permanganate oxidation.

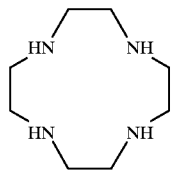

30 g (0.15 mol) of 2a,4a,6a, 8a-decahydro-tetraaza-cyclopent[fg]acenaphthylene (prepared according to Examples 1, 2 or 3), are dissolved in 200 mL of water. The solution is cooled to 0° C. and a 5%-potassium permanganate aqueous solution (750 g of solution, 0.30 mol) is dropwise added. Then manganese dioxide is filtered on a bed of celite under vacuum. The filtrate is transferred to the autoclave, 48 g of sodium hydroxide are added and the solution is heated to 180° C. for 24 h then cooled. The content of the autoclave is transferred to a common reactor. The suspension is heated to ebullition, and treated with active carbon by filtering the hot solution on a bed of celite under vacuum. The filtrate is concentrated of 50° C. under reduced pressure, to give a turbid solution which is cooled to 25° C. under stirring. After one night the crystallized solid is filtered and dried in an oven under vacuum, up to a constant weight to give 10.9 g of highly pure 1,4,7,10-tetraazacyclododecane (1st crop) (99.6%, GC), as a white needle-shaped crystalline product.

The mother liquors are concentrated to 50° C. under reduced pressure to give a turbid solution which crystallizes under the same conditions of the 1st crop thus giving additional 2.8 g of 1,4,7,10-tetraazacyclododecane (2nd crop) (98.5%, GC). Total yield: 52%. $^1$H—NMR, $^{13}$C—NMR, IR and MS spectra are consistent with the structure.

According to the procedure described in the example the following tetraazamacrocycles starting from the tetracycles prepared following Example 1, 2 or 3 are prepared:

-1,4,7,10-tetraazacyclotridecane

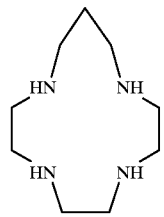

-1,4,8,11-tetraazacyclotetradecane

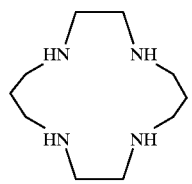

-1,4,8,12-tetraazacyclopentadecane

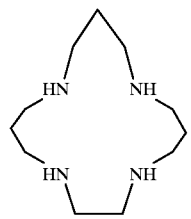

EXAMPLE 5

Preparation of 1,4,7,10,-tetraazacyclododecane through oxidation of 2a,4a,6a,8a-decahydro-tetraazacyclopent [fg]acenaphthylene with hypochlorite

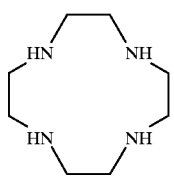

30 g (0.15 mol) of 2a,4a,6a,8a-decahydro-tetraazacyclopent[fg]acenaphthylene, dissolved in 300 g of water, are treated with 550 g (0.89 mol) of sodium hypochlorite (approx. 12% aqueous solution) for 24 h at 80° C. The final solution is cooled and hydrolyzed under conditions analogous to those described in Example 4. 9.8 g (1st and 2nd crop) of 1,4,7,10-tetraazacyclododecane are obtained. Yield: 38%.

EXAMPLE 6

Preparation of 1,4,7,10-tetraazacyclododecane through oxidation of 2a,4a,6a,8a-decahydro-tetraazacy-clopent [fg] acenaphthylene with persulfate.

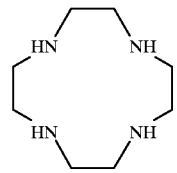

30 g (0.15 mol) of 2a,4a,6a,8a-decahydro-tetraazacyclopent [fg]acenaphthylene, dissolved in 700 g of water, are treated with 620 mL of 2N NaOH. To the resulting solution, cooled to 0° C., are added 71.4 g (0.3 mol) of sodium persulfate dissolved in 700 mL of water. After 1 h the solution is hydrolyzed, following the procedure of Example 4 to give 8.7 g (0.5 mol) of 1,4,7,10-tetraazacyclododecane. Yield: 33%.

EXAMPLE 7

Preparation of 1,4,7,10-tetraazacyclododecane through oxidation of 2a,4a,6a,8a-decahydro-tetraazacyclopent [fg] acenaphthylene with bromine in acetic buffer.

26 g (0.13 mol) of 2a,4a,6a,8a-decahydro-tetraazacyclopent [fg]acenaphthylene are dissolved in 1.3 L of sodium hydroxide 2N. The solution is buffered to pH 5 through addition of 300 g of acetic acid, then 43.8 g (0.27 mol) of bromine are dropwise added and kept for 2 h at 25° C. 200 g of sodium hydroxide are added and the solution is heated in autoclave at 150° C. for 24 h, then the solution is cooled and concentrated up to 400 mL. The product crystallizes at room temperature (25° C.) for one night to give 8.7 g of 1,4,7,10-tetraazacyclododecane.

Yield: 38%

EXAMPLE 8

Preparation of 1,4,7,10-tetraazacyclododecane through oxidation of 2a,4a,6a,8a-decahydro-tetraazacy-clopent [fg] acenaphthylene with air 20 g (0.10 mol) of 2a,4a,6a,8a-decahydro-tetraazacyclopent [fg]acenaphthylene are dissolved in 100 g of sulfuric acid (water content=50%). Air is bubbled into the solution, which is heated to ebullition (T=112° C.) for 24 h, and then is cooled. 170 g of 30%-water sodium hydroxide are slowly added and the suspension is kept at a temperature of 17° C. for a whole night.

Crude 1,4,7,10-tetraazacyclododecane is filtered and dried in oven under vacuum. The resulting 5.6 g of crude product are redissolved in 50 mL of warm toluene. The insoluble salts are filtered and the filtrate is concentrated up to a volume of 10 mL and kept at 17° C. per 2 h to give 3.8 g of purified 1,4,7,10-tetraaza-cyclododecane.

Yield: 22%

EXAMPLE 9

Preparation of 1,4,7,10-tetraazacyclododecane through oxidation of 2a,4a,6a,8a-decahydro-tetraazacy-clopent [fg] acenaphthylene with bromine.

1.66 kg (8.55 mol) of 2a,4a,6a,8a-decahydro-tetra-azacyclopent [fg]acenaphthylene (prepared according to Examples 1 and 2) are dissolved in 15 kg of deionized water. 18.5 kg of 1N HCl are added up to pH 4.5, then the solution is cooled to 20° C. and 3.42 kg of bromine (21.48 mol) and 46.7 kg of 1N NaOH are dropwise added to keep pH 4.5.

After one night at room temperature 8.4 kg of NaOH are added, up to pH 14. The solution is transferred to the autoclave and hydrolyzed at 180–185° C. for 5.5 h then cooled to room temperature. The solution is concentrated under reduced pressure. The resulting suspension is kept under stirring at room temperature for 24 h, then the precipitate is filtered. The wet solid is dried in an oven under vacuum to give 1,4,7,10-tetraazacyclododecane contaminated by inorganic salts. The solid is suspended in 16 kg of toluene and heated under reflux, the water is removed through azeotropic distillation and then the suspension volume is reintegrated with fresh toluene. The inorganic salts are removed by filtering the hot solution, and washed with toluene preheated at 60° C. The filtrate is concentrated up to a residual weight of 3 kg, then cooled to 17° C. for 2 h and up to 0C. for 1 h. The crystallized solid is filtered and washed with few cold toluene and the product is dried at 50° C. under vacuum to give 0.9 kg (5.22 mol) of 1,4,7,10-tetraazacyclododecane (GC: 99.23%). From toluene mother liquors, concentrated to 250 mL, 108 g (0.63 mol) are obtained as second crop.

Total yield: 68%.

EXAMPLE 10

Preparation and isolation of the compound of formula (XIV)

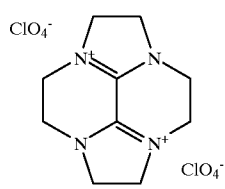

(XIV)

50.4 g (0.259 mol) of 2a,4a,6a,8a-decahydro-tetraazacyclopent [fg]acenaphthylene are dissolved in 955 g of deionized water. 311 g of iN HCl are added up to pH 4.5, then the solution is cooled to 20° C. and 91.44 g (0.66 mol) of bromine and 1.026 kg of 1N NaOH, are simultaneously dropwise added in order to keep a pH of 4.5. After one night at room temperature the solution is concentrated under reduced pressure and at 50° C. up to 1.38 kg. Then is cooled to 25° C. and 144 g of aqueous solution containing 50% w/w of sodium perchloride monohydrate are added under stirring. After 15 h the precipitate is filtered and washed with water. After drying in oven under vacuum at 50° C., 50.5 g of the product are obtained. Yield: 50%. Electrophoretic method Capillary: fused silica 0.56 m×75 mm Voltage: 12 kV Buffer: 0.05 M phosphate pH 4.5 Temperature: 40° C. Stoptime: 20 min. Detection: (UV) 200–220 nm Injection: hydrostatic (50 mbar, 3s) Sample conc.: 1 mg/mL Instrumentation: Hewlett Packard 3D HPCE

| Preconditioning timetable: | t (min) | action |
|---|---|---|
| | 0 | flush with H$_2$O |
| | 2 | flush with 0.1M NaOH |
| | 4 | flush with H$_2$O |
| | 5 | flush with buffer |
| | 9 | start analysis |

EXAMPLE 11

Preparation of 1,4,7,10-tetraazacyclododecane through hydrolysis of the product of Example 10

| Elemental analysis | C % | H % | Cl % | N % | O % |
|---|---|---|---|---|---|
| calc. | 30.70 | 4.12 | 18.13 | 14.32 | 32.72 |
| found | 30.74 | 4.14 | 18.03 | 14.20 | 32.66 |

45g (0.115 mol) of compound (XIV) (prepared according to Example 10), are suspended in 1.1 L of water. NaOH is added up to pH 14, the suspension is transferred to the autoclave and saponificated to 185° C. for 5.5 h. The solution is cooled to 50° C. and concentrated under reduced pressure up to 0.75 L and kept for 24 h at room temperature and filtered. The precipitated solid is filtered and dried to give 1,4,7,10-tetraazacyclododecane contaminated by inorganic salts, then purified through recrystallization from toluene, as described in Example 9 to give 16.8 g (0.098 mol, 1st crop) of 1,4,7,10-tetraazacyclododecane (GC: 99.5%).

EXAMPLE 12

Oxidation of 2a,4a,6a, 8a-decahydro-tetraazacyclopent-[fg]acenaphthylene with sodium bisulfite.

40 g (0.206 mol) of 2a,4a,6a, 8a-decahydro-tetraazacyclopent[fg]acenaphthylene are dissolved in 500 g of water. 86 g of sodium bisulfite (0.824 mol) are added and the solution is heated to 95° C. for 17 h then cooled to room temperature. NaOH is added up to 14 and then the procedure is carried out according to Example 9 to give 15.9 g (0.093 mol) of 1,4,7,10-tetraazacyclododecane (GC: 98.5%). Yield: 45%.

EXAMPLE 13

Preparation of compound (XV)

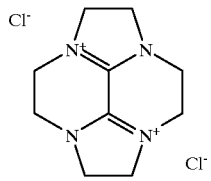

(XV)

4.12 g of (XIV) (see Example 10), are dissolved in 410 mL of deionized water. The solution is percolated on a column containing 136 mL of Amberlite 4200 resin (Cl⁻ form), and then washed with water. The useful fractions containing the product (TLC analysis (silica gel) :eluent:chloroform:acetic acid:water=4:5:1 (v/v/v)) are collected and concentrated at 50° C. under vacuum, up to a small volume, then isopropanol is added. After 4 h the precipitate is filtered and washed on a filter with few isopropanol. After drying the product in an oven under vacuum at 50° C., 2.14 g of the desired product are obtained. Analytical characteristics: Water content (karl fischer): 11.8% AgNO$_3$(Cl⁻): 99% (calculated for the anhydrous)

We claim:

1. A process for the preparation of tetraazamacrocycles of the formula:

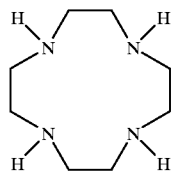

(VIII)

comprising the following steps of the following Scheme:

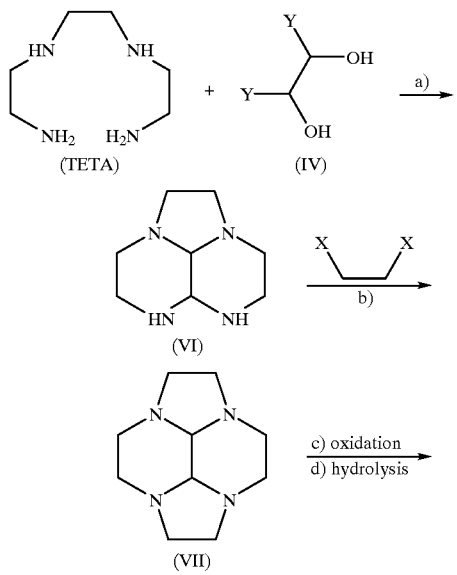

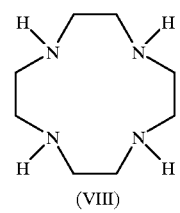

(VIII)

wherein step (a): condensing tetraazacenaphthylene (TETA) with the glyoxal derivative of formula (IV), wherein Y is —OH (glyoxal hydrate) or [—SO$_3$—Na⁺] (Bertagnini's salt), in a water or in water-soluble solvent or a mixture thereof, at a temperature of 0–50° C., in the presence of a stoichiometric amount or slight excess of calcium hydroxide, to give the compound of formula (VI);

step (b): condensing the compound of formula (V) with an alkylating agent X—CH$_2$—CH$_2$—X, wherein X is a halogen or a sulfonic acid reactive derivative, in at least stoichiometric amounts, in the presence of at least 2 moles of a base selected from alkali or alkaline-earth metal carbonates per mol of compound (VI), at a temperature of 25–150° C., to give the compound of formula (VII);

step (c): oxidizing the compound of formula (VII) with an oxidizing agent, in water or in a diphasic system of water and an organic solvent, resistant to oxidation, at a temperature of 0–100° C., to give a mixture of oxidated products and thereafter;

step (d): hydrolyzing the product of step (c) in acid aqueous solution at a pH lower than 2 or in a basic aqueous solution at a pH higher than 12, at a temperature of 110—200° C., to give the compound of formula (VIII).

2. The process according to claim 1, in which the oxidizing agent used in step (c) is selected from the group consisting of high oxidation state transition metals derivatives, halogen derivatives having a positive oxidative state, halogens, peroxides, peracid salts and oxygen in acid solution.

3. The process according to claim 1 in which the oxidizing agent used in step (c) is selected from the group consisting of potassium permanganate, sodium hypochlorite, bromine and chlorine, hydrogen peroxide, sodium persulfate, oxygen in solution of concentrated sulfuric acid and sodium bisulfite.

4. The process according to claim 1, in which the oxidizing agent in step (c) is bromine in slightly acidic aqueous solution.

5. The process according to claim 1, in which the alkylating agent used in step (b) is selected from the group consisting of 1,2-dibromoethane and 1,2-dichloroethane.

6. The process according to claim 1, in which the oxidizing agent used in step (c) is bromine in aqueous solution at pH 4–5, in a ratio of 2–3 moles of bromine per mol of compound (VII), at a temperature ranging from 17 to 30° C.

7. The process according to claim 6, in which the pH of the bromine aqueous solution is 4.5 and bromine is added in a ratio of 2.5 mol per mol of compound (VII).

* * * * *